US005801063A

United States Patent [19]
Grandics et al.

[11] Patent Number: 5,801,063
[45] Date of Patent: Sep. 1, 1998

[54] DEVICE AND PROCESS FOR THE BIOSPECIFIC REMOVAL OF HEPARIN

[76] Inventors: Peter Grandics; Susan Szathmary, both of P.O. Box 1924, Arcadia, Calif. 91077

[21] Appl. No.: 437,891

[22] Filed: May 9, 1995

[51] Int. Cl.$^6$ .............. A61M 37/00; A61M 1/30; G01N 33/543

[52] U.S. Cl. .............. 436/518; 436/523; 436/529; 436/533; 436/541; 436/807; 435/2; 435/284.1; 435/288.6; 435/962; 422/56; 422/59; 422/73; 604/4; 604/5; 604/6; 604/7; 604/19

[58] Field of Search .............. 604/4–6, 7, 19; 422/56, 59, 73; 435/2, 284.1, 288.6, 962; 436/518, 523, 529, 533, 541, 807

[56] References Cited

U.S. PATENT DOCUMENTS

| | | | |
|---|---|---|---|
| 4,200,690 | 4/1980 | Root et al. | 435/7 |
| 4,326,532 | 4/1982 | Hammar | 128/349 R |
| 4,411,786 | 11/1983 | Russell | 210/321.3 |
| 4,450,104 | 5/1984 | Jordan . | |
| 5,229,268 | 7/1993 | Pry et al. | 435/7.92 |

FOREIGN PATENT DOCUMENTS

PCT/US96/
06515  8/1996  WIPO .

OTHER PUBLICATIONS

Hook et al., FEBS Letters, vol. 66 (1), pp. 90–93, Jul. 1976.
Jorpes J.E., Heparin in the Treatment of Thrombosis, pp. 100–104 and 116–129, 1946.
Wattrisse et al., Thrombosis Research, vol. 65 (1), S177—Abstract Only. 1992.

V. S. Hornsey et al., "Reductive Amination for Solid–Phase Coupling of Proteins", *J. Immunol. Meth.* 93: 83–88 (1986).

J. Porath, "General Methods and Coupling Procedures", *Meth. Enzymol.* 34: 13–30 (1974).

*Primary Examiner*—Christopher L. Chin
*Assistant Examiner*—Bao-Thuy L. Nguyen
*Attorney, Agent, or Firm*—Merchant, Gould, Smith, Edell, Welter & Schmidt

[57] ABSTRACT

A method and device is described for direct removal of heparin from whole blood during extracorporeal therapy. In clinical situations where the blood is heparinized to prevent clotting in the extracorporeal circuit containing e.g., a hemodialysis cartridge or a heart-lung machine, it would be desirable to eliminate the systemic heparinization of the patients. The extracorporeal circuit contains a device having antithrombin III immobilized and inserted between the outlet port of the primary extracorporeal device, such as the hemodialysis cartridge or heart-lung machine and the patient. When the heparinized blood comes in contact with the immobilized antithrombin III, heparin is removed and the reperfused blood is substantially free of heparin. The advantage of the system lies in the fact that heparin is removed from the blood rather than neutralized. This helps overcome the adverse reactions and side effects associated with the use of heparin anticoagulation.

16 Claims, No Drawings

DEVICE AND PROCESS FOR THE BIOSPECIFIC REMOVAL OF HEPARIN

BACKGROUND OF THE INVENTION

This invention describes an extracorporeal blood treatment method wherein heparin is removed from an extracorporeal blood flow by using a device containing antithrombin III immobilized to a support matrix.

The highly sulfated glycosamino glycan, heparin, is the most widely used clinical anticoagulant. Its numerous clinical applications include prophylactic treatment of high-risk embolic patients; post-operative prevention of thromboembolism; treatment of thromboembolic patients; and the prevention of blood clotting as well as the formation of thrombi resulting from interventions, such as cardio-vascular diagnostic procedures, surgery of the heart and blood vessels, and catheterization. Other important applications include extracorporeal blood circulation, such as hemodialysis, plasmapheresis and blood oxygenation. Heparin is also used during implantation of artificial organs and organ (e.g. kidney) transplantation.

It is estimated that approximately twenty million procedures involving extracorporeal blood circulation are performed annually. Approximately 10,000 renal transplantations are performed annually in the U.S. along with about 500,000 open heart surgeries, both procedures requiring extracorporeal blood treatment In addition, approximately ninety thousand plasmapheresis procedures are carried out annually in the U.S. Blood oxygenation has been used to treat patients suffering from acute respiratory failure and infants with diaphragmatic hernia. It is likely that new procedures which are in development, such as the implantation of artificial hearts and artificial livers, will increase the use of extracorporeal circulation.

In all of these procedures, blood is drawn from the patient and passed through an extracorporeal circuit. During contact with the materials of the extracorporeal devices, the blood's strictly regulated hemostasis is upset, and thus the blood tends to clot within the device. The thrombi formed block the perfusion through the device. The use of heparin, which is the most widely used anticoagulant, prevents clotting and maintains fluidity in extracorporeal circulation. The heparin (10,000–30,000 units) is systemically administered to the patient and the extracorporeal circuit prior to treatment. This high level of heparin administration poses a significant hemorrhagic risk. Heparinization is linked to eight to thirty percent of all the hemorrhagic complications. Bleeding complications were reported in ten percent of the patients, having a high risk of hemorrhage, receiving low dose heparin treatment. Also, nineteen percent of these patient receiving regional heparin anticoagulation developed bleeding complications.

It is estimated that approximately twenty five percent of all patients with acute renal failure had increased bleeding risk during and right after dialysis. Bleeding complications are more frequent for patients who recently have undergone cardiac or vascular surgery and with multiple traumata. In addition, patients who have undergone open heart surgery exhibit a six to ten percent incidence of coagulation abnormalities along with excessive post-operative bleeding.

There are also a number of other complications linked to heparinization, such as thrombocytopenia, alopecia, and interference with bone repair and maintenance. These complications become evident when the drug is administered over a long period of time and link heparin to the majority of drug deaths in patients who are reasonably healthy.

Significant effort has been spent at solving the problem of life-threatening hemorrhage associated with systemic heparinization. One widely used approach in clinics includes the use of anti-heparin compounds, such as protamine. In protamine neutralization, heparin's anticoagulant effect is blocked with a precisely determined dosage of protamine sulfate. In open heart surgery, as much as 150–300 mg of protamine may be required for heparin neutralization. The dosage of protamine must be very precise because excess protamine may interfere with the coagulation assays. Additional complications derive from the protamine sulfate's side effects and may contribute to the patient's morbidity and/or mortality. Common side effects include vasodilation, decreased cardiac output, hypotension, decreased peripheral vascular resistance, dyspnea, increased or decreased pulmonary arterial resistance, bleeding, decreased arterial $pO_2$, or complement activation (promoted by the heparin-protamine complex). The major adverse reaction is anaphylactic shock.

During surgery, the majority of protamine related adverse reactions occur immediately. It would be desirable to have a device capable of removing all the heparin (approximately 10,000–30,000 units) at the termination of the operation. Also, it would be desirable if such a device could operate at flow rates of about 1–2 liters/minute with a total device volume of about 200–1,000 ml. With such a device, the time and costs associated with adverse protamine reactions could be eliminated. Another approach in the prior art to overcoming heparin's effects is the introduction of new antithrombotic agents, such as low molecular weight heparins and heparin substitutes like prostacyclin. Low-dose heparinization or regional anticoagulation has also been introduced. This is performed by infusion of protamine into the heparinized blood at the return side of the extracorporeal circuit Regional citrate anticoagulation was also developed during which citrate is used as the anticoagulant and calcium is used as a citrate neutralizing agent.

Repligen Corporation conducted studies to evaluate the role of platelet factor 4 (PF4) in heparin neutralization. PF4 is a very effective heparin antagonist. It is chemotactic for neutrophils and monocytes and it is assumed that the platelets mediate inflammatory reactions by PF4 release. During clinical examinations the PF4 injections resulted in serious granulocytopenia in humans. Another method in the prior art describes an immobilized heparinase filter to degrade heparin at the end of extracorporeal circulation. Heparinase is a heparin catabolizing enzyme and was shown to neutralize the anticoagulant effects of heparin. Heparinase is unstable and loses activity easily. Its introduction into the circulation can lead to acute or chronic immunological responses. This is particularly important since immobilized heparinase can leach off of the support materials. In addition, it is difficult to sterilize or store the heparinase enzyme reactor without significant loss of enzyme activity.

None of the above approaches led to a satisfactory, simple clinical solution to the problem of extracorporeal anticoagulation. The serious or even fatal anaphylactic reactions to intravenous protamine administration have been well documented. The use of low molecular weight heparins as new anti-thrombotic agents have not shown significant improvement over traditional unfractionated heparins and are even more difficult to neutralize than unfractionated heparin. Low-dose heparinization proved unsatisfactory in providing adequate anticoagulation in extracorporeal therapies. Regional heparin anticoagulation still requires protamine as the neutralizing agent. Regional citrate anticoagulation is rarely used because of the technical difficulties in performing the procedures and in determining the adequate amount of calcium required for citrate neutralization. Prostacyclin administration is associated with sudden, unpredictable hypotension. The use of PF4 in clinical heparin neutralization seems unlikely due to the unfavorable clinical trial results. The objective of this invention is to develop a simple and effective device for removing heparin from extracorporeal circuits. Another objective of this invention is to prevent blood clotting in the extracorporeal circuit, without introducing heparin into the patient. Also, the invention attempts to reduce the likelihood of hemorrhagic complications associated with the use of heparin. The subject invention removes heparin from extracorporeal blood by the use of immobilized antithrombin III. A further objective of this invention is to prevent the toxic effects of protamine resulting from heparin neutralization with protamine.

SUMMARY OF THE INVENTION

The subject invention provides an extracorporeal device for treating blood or plasma which device has an inlet for receiving heparinized blood and an outlet for discharging substantially heparin-free blood. As described by the invention, purified antithrombin III is immobilized to a chromatography support packed into a column device which allows sufficient contact of the particles with the heparinized blood. Such contact results in the removal of heparin from the blood. The purified antithrombin III should be of clinical grade and preferably approved as a parenteral therapeutic by the Food and Drug Administration. It can derive from a natural source, such as human plasma or can be produced by recombinant DNA technology. As suggested, antithrombin III is immobilized to a chromatography support by covalent linkages. The support may be a polymer matrix which having a substantial number of reactive groups, such as aldehyde, hydroxyl, thiol, carboxyl or amino groups, which can be activated for coupling antithrombin III. A polymer support matrix may include natural carbohydrates, such as agarose, cellulose or dextran or synthetic polymers including polystyrene, polyethersulfone, PVDF, ethylene vinyl alcohol, polycarbonate, polyether, polyethercarbonate, regenerated cellulose, cellulose acetate, polylactic acid, nylon, or polyurethane.

The heparin removing device is used in conjunction with another extracorporeal device, such as an artificial kidney or an artificial heart-lung device. In this scenario, heparin is added to the blood flow which passes through the extracorporeal device, thereby preventing coagulation and the formation of thrombi. The heparinized, treated blood is then passed through the deheparinization device containing antithrombin III which removes heparin and the blood is then returned to the patient free of heparin.

The subject invention allows for regional heparinization, as it removes heparin from the blood rather than neutralizing the anticoagulant effects of heparin. This helps minimize heparin's toxic side effects. The immobilization matrix must meet several criteria in order to be compatible with blood. First, it must be biocompatible and must contain the functional groups to immobilize antithrombin III. Secondly, it must be stable chemically to avoid breakdown in the blood. It must have appropriate pressure-flow characteristics as well as sufficient mechanical stability to withstand the conditions of extracorporeal circulation. The support material must not cause hemolysis, platelet activation/ aggregation, thrombus formation, activation of white blood cells and the complement system and must be nontoxic. We describe here various procedures that can be applied to produce such an extracorporeal deheparinization system.

DETAILED DESCRIPTION

In the prior art, the patient's blood is circulated through an extracorporeal device, such as an artificial kidney or a heart-lung machine. Circulation is completed by returning the blood from the extracorporeal device to the patient. The patient's blood is heparinized by the infusion of heparin right before the extracorporeal device. The heparin can be given either systemically to the patient or continuously infused into the blood passing through the device. The blood returning to the patient thus contains heparin which in some procedures is neutralized by infusion of protamine. The heparin-protamine complex strongly activates the complement system. Heparin rebound has also been reported after a certain period of time following protamine administration.

In the subject invention, the patient's blood is heparinized, just like in the prior art, right before the extracorporeal device which can be an oxygenator or a hemodialysis cartridge. However, a novel extracorporeal device is inserted between the oxygenator or a hemodialysis cartridge and the patient. The device contains immobilized antithrombin III which removes the heparin from the blood returning to the patient Since the antithrombin III is immobilized, the returning blood is both heparin and antithrombin III free.

As a result of this, the patient never comes in contact with heparin during the extracorporeal therapy. This should reduce the hemorrhagic risks associated with heparin administration. The device may be a filter cartridge to which antithrombin III is immobilized. Alternatively, the antithrombin III is immobilized directly on a hemofilter or the hemodialyzer equipment. Another possible arrangement is to immobilize antithrombin III to large bead chromatography particles which have a substantial interparticle channel structure. Cellular elements in the blood can flow through these channels without restriction. The terminology of "device" should be interpreted broadly to indicate any means of removing and retaining undesired heparin from the blood prior to reintroduction into the patient. Biocompatibility of the matrix is an important issue. We believe that the immobilized antithrombin III will provide a substantially biocompatible surface.

The support matrix must have reactive functional groups, such as, but not limited to, aldehyde, hydroxyl, thiol, amino or carboxyl groups, available for protein coupling. Other reactive functional groups for coupling proteins are well known in the art. Also, the support should be activatable to bind antithrombin III. It should be emphasized, however, that other still undiscovered biomaterials could be utilized in the novel heparin removing system along with novel activation methods and coupling procedures suitable to immobilize antithrombin III.

An example of immobilization of antithrombin III is to a cellulose support matrix, such as a regenerated cellulose hollow fiber membrane which is used in hemodialyzers. Cellulose contains abundant hydroxyl groups which can be activated with sodium metaperiodate, thus oxidizing them to aldehyde groups. In a specific example, a small hollow fiber cartridge (approximately 15 cm in length) is used. The cellulose fibers are activated by perfusing the cartridge with 150 ml of 10 mM sodium metaperiodate solution for 10 minutes. The bundle of fibers is then extensively washed with deionized water. Antithrombin III is then coupled by reductive amination (as described by Hornsey et al. (1986), J. Immunol. Methods 93. pp. 83–88) from a 100 ml coupling solution containing 2 mg/ml protein. Aldehyde derivatization of other supports, such as polystyrene, polyethersulfone, PVDF, ethylene vinyl alcohol, polycarbonate, polyether, polyethercarbonate, polylactic acid, nylon, or polyurethane can be performed with formaldehyde or glutaraldehyde using standard chemical reactions (reviewed in Affinity Techniques, Methods in Enzymology Vol. 19A).

It was an unexpected observation that the Cellthru Bigbead™ media, 300–500 μm beads, (Sterogene Bioseparations, Inc., Carlsbad, Calif., USA) allowed passing a very high solid content and viscous fluid, such as blood with a hematocrit of approximately 40%, through a packed column bed. It was also observed that the Bigbeads allow highly efficient immobilization of antithrombin III with the retention of most of its heparin binding activity. This allowed, for the first time, the manufacture of a high capacity column device for direct blood purification. Antithrombin III was immobilized onto the novel aldehyde activated 4% agarose beads (300–500 μm particles) trademarked as LS Activated ALD Cellthru Bigbeads (Sterogene Bioseparations, Inc., Carlsbad, Calif., USA) at 5 mg/ml following the manufacturer's directions. Packed columns allow significantly higher capacities than membrane-based devices and are fairly insensitive to fouling by a highly protein rich medium, such as plasma.

In an alternative procedure, antithrombin III is oxidized with 1 mM $NaIO_4$ at 0° C. for 5 min and then coupled to Amino Cellthru Bigbeads (300–500 μm particles), manufactured by Sterogene Bioseparations Inc., Carlsbad, Calif., USA, at 5 mg/ml following the manufacturer's directions. The following experiments demonstrated that immobilized antithrombin III, packed into a column cartridge, behaves similarly to free antithrombin III in terms of its ability to bind heparin from whole blood and plasma.

Human AT III derivatized 300–500 μm Cellthru BigBeads were packed into 1.0 ml columns and perfused with 12 ml of fresh human blood spiked with 0.45 U/ml of heparin. The flow rate was 1.0 ml/min, i.e., 1 bed volume per minute. Such a high loading velocity is important in light of the volume of blood which need to be perfused through such a device within the specified time frame of the extracorporeal therapy. The heparin activity was determined by the Chromogenix LMW Heparin/Heparin Assay. The heparin activity in the collected flow-through was reduced below 0.05 U/ml. In identical experiments, 5.0 U/ml heparin was also removed from blood. The resin reduced the LMWH activity in the same manner which is notable since protamine cannot neutralize low-molecular-weight heparin. When the same experiments were repeated with citrated fresh-frozen plasma, very similar results were obtained. These results give indication that the technology permits sufficient heparin reduction in therapeutic situations, and that the antithrombin III-modified surface of the Bigbead particles bound with the removed heparin may provide an antithrombotic surface. In separate experiments, the antithrombin III-derivatized particles were tested for hemolysis. Anticoagulated fresh human blood was perfused through the test columns at the flow rate of one bed volume per minute and free hemoglobin was measured before and after the column. The free hemoglobin levels were below 30 mg/dl (normal range <30 mg/dl) which demonstrated that the erythrocytes were not damaged during their passage through the column device. White blood cells and platelet aggregation was also tested. The white blood cell and platelet counts remained in the normal range (6000/mm$^3$ and 200,000/mm$^3$, respectively) following perfusion of blood through the column device.

Accordingly, a system for extracorporeal treatment of whole blood according to the present invention can comprise:

(1) two extracorporeal devices, a first extracorporeal device and a second extracorporeal device, connected in-line; and (2) means for introducing a precisely controlled flow of heparin into an extracorporeal blood circuit prior to the blood entering the first extracorporeal device.

The second device contains antithrombin III covalently immobilized to a biocompatible polymer matrix for binding the heparin. The second device is inserted between the first device and a return line of the blood to a living being, so that the heparin is substantially removed from the returned blood.

Typically, the biocompatible matrix is selected from the group consisting of agarose, cellulose, dextran, polystyrene, polyethersulfone, PVDF, ethylene vinyl alcohol, polycarbonate, polyether, polyethercarbonate, regenerated cellulose, cellulose acetate, polylactic acid, nylon, and polyurethane.

The polymer matrix can be in the form of a membrane. Alternatively, the polymer matrix can be in the form of large particles; in this alternative, the size of the large particles is preferably greater than about 300 μm. The large particle polymer matrix has reactive groups bound thereto; typically, the reactive groups are selected from the group consisting of aldehyde, hydroxyl, thiol, carboxyl and amino groups.

Another embodiment of the present invention comprises:

(1) a device selected from the group consisting of an artificial heart-lung device and a hemodialysis unit;

(2) an outlet coupled to said device for receiving heparinized blood;

(3) a support matrix formed of a blood compatible material and having antithrombin III immobilized thereon for removing heparin from the blood, the support matrix receiving heparinized blood from the outlet; and (4) means for reintroducing the blood, substantially free of heparin, into a living being.

In addition to heparinization, there are many situations requiring removal of toxins or other chemical species from blood. It is an objective of this invention to provide a multipurpose technique for treatment of fragile biological solutions including whole blood by continuous removal of undesired substances at relatively high flow rates. It is also an objective to provide such a method and devices utilizing bioactive substances immobilized on a blood-compatible support matrix which is mechanically and chemically stable. In addition, there are numerous industrial or research processes, such as some fermentation processes, where on-line product removal is desirable but not achievable due to the fragile character and high density of the cells and the required high flow rates.

The novel heparin removing system can be applied to a wide variety of clinical situations, such as plasmapheresis, extracorporeal membrane oxygenation, hemodialysis, hemofiltration, open heart surgery, organ transplantation, etc. Accordingly, it is to be understood that the description in this disclosure is to facilitate comprehension of the invention and should not be construed to limit the scope thereof as persons skilled in the art can, in light of this disclosure, can generate additional embodiments without exceeding the scope or departing from the spirit of the claimed invention.

We claim:

1. A system for extracorporeal treatment of heparinized whole blood comprising:

(a) two extracorporeal devices, a first extracorporeal device and a second extracorporeal device, connected in-line; and (b) means for introducing a precisely controlled flow of heparin into an extracorporeal blood circuit prior to the blood entering the first extracorporeal device; the second device containing antithrombin III covalently immobilized to a biocompatible polymer matrix for binding said heparin, the second device being inserted between the first device and a return line of the blood to a living being, so that said heparin is removed from the returned blood.

2. The system of claim 1 wherein said biocompatible matrix is selected from the group consisting of agarose, cellulose, dextrin, polystyrene, polyethersulfone, polyvinyl difluoride, ethylene vinyl alcohol, polycarbonate, polyether, polyethercarbonate, regenerated cellulose, cellulose acetate, polylactic acid, nylon, and polyurethane.

3. The system of claim 1 wherein said polymer matrix is in the form of a membrane.

4. The system of claim 1 wherein said polymer matrix is in the form of large particles.

5. The system of claim 4 wherein the size of the large particles is greater than about 300 μm.

6. The system of claim 5 wherein said large particle polymer matrix has reactive groups bound thereto.

7. The system of claim 6 wherein the reactive groups are selected from the group consisting of aldehyde, hydroxyl, thiol, carboxyl and amino groups.

8. An extracorporeal apparatus for treating heparinized whole blood, comprising:

(a) a device selected from the group consisting of an artificial heart-lung device and a hemodialysis unit;

(b) an outlet coupled to said device for receiving heparinized blood;

(c) a support matrix formed of a blood compatible material and having antithrombin III immobilized thereon for removing heparin from the blood, the support matrix receiving heparinized blood from the outlet; and (d) means for reintroducing the blood, free of heparin, into a living being.

9. A system for extracorporeal treatment of heparinized whole blood comprising:

(a) two extracorporeal devices, a first extracorporeal device and a second extracorporeal device, connected in line; and (b) means for introducing a precisely controlled flow of heparin into an extracorporeal blood circuit prior to the blood entering the first extracorporeal device; the second device containing antithrombin III covalently immobilized to a biocompatible polymer matrix through the carbohydrate moiety of the antithrombin III for binding said heparin, the second device being inserted between the first device and a return line of the blood to a living being, so that said heparin is removed from the returned blood.

10. The system of claim 9 wherein said biocompatible matrix is selected from the group consisting of agarose, cellulose, dextrin, polystyrene, polyethersulfone, polyvinyl difluoride, ethylene vinyl alcohol, polycarbonate, polyether, polyethercarbonate, regenerated cellulose, cellulose acetate, polylactic acid, nylon, and polyurethane.

11. The system of claim 9 wherein said polymer matrix is in the form of a membrane.

12. The system of claim 9 wherein said polymer matrix is in the form of large particles.

13. The system of claim 12 wherein the size of the large particles is greater than about 300 μm.

14. The system of claim 13 wherein said large particle polymer matrix has reactive groups bound thereto.

15. The system of claim 14 wherein the reactive groups are selected from the group consisting of aldehyde, hydroxyl, thiol, carboxyl, and amino groups.

16. An extracorporeal apparatus for treating heparinized whole blood, comprising:

(a) a device selected from the group consisting of an artificial heart-lung device and a hemodialysis unit;

(b) an outlet coupled to said device for receiving heparinized blood;

(c) a support matrix formed of a blood compatible material and having antithrombin III immobilized thereon through the carbohydrate moiety of the antithrombin III for removing heparin from the blood, the support matrix receiving heparinized blood from the outlet; and (d) means for reintroducing the blood, free of heparin, into a living being.

* * * * *